United States Patent [19]

Kondo et al.

[11] 4,340,672
[45] Jul. 20, 1982

[54] ENZYMATIC SYNTHESIS OF β-LACTAM ANTIBACTERIALS

[75] Inventors: Eiji Kondo, Ikeda; Takashi Mitsugi, Izumiotsu; Tamio Fujiwara, Amagasaki; Ryonosuke Muneyuki, Kyoto, all of Japan

[73] Assignee: Shionogi & Co., Ltd., Osaka, Japan

[21] Appl. No.: 188,869

[22] Filed: Sep. 19, 1980

[30] Foreign Application Priority Data

Sep. 19, 1979 [JP] Japan .................................. 54-119260

[51] Int. Cl.$^3$ .............................................. C12P 37/04
[52] U.S. Cl. ......................................... 435/45; 435/50
[58] Field of Search .................................... 435/45, 50

[56] References Cited

U.S. PATENT DOCUMENTS

| | | | |
|---|---|---|---|
| 3,787,288 | 1/1974 | Miyamura et al. | 435/45 |
| 3,945,888 | 3/1976 | Takahashi et al. | 435/50 |
| 4,073,687 | 2/1978 | Kondo et al. | 435/50 |

*Primary Examiner*—Alvin E. Tanenholtz
*Assistant Examiner*—James Martinell
*Attorney, Agent, or Firm*—Birch, Stewart, Kolasch & Birch

[57] ABSTRACT

Penicillins and cephalosporins can be synthesized by the action of an acylase on a penicillin or cephalosporin nucleus amine as substrate and an ester (I) of the following formula as the acyl source:

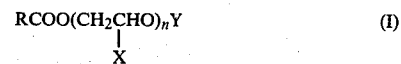

(wherein
RCO is an acyl group in penicillin or cephalosporin side chains;
X is a hydrogen atom, lower alkyl group or hydroxy-lower alkyl group;
Y is a hydrogen atom or a lower alkyl group; and n is a positive integer).

The novel acyl source (I) is also disclosed.

3 Claims, No Drawings

ENZYMATIC SYNTHESIS OF β-LACTAM ANTIBACTERIALS

BACKGROUND AND SUMMARY OF THE INVENTION

This invention is related to a novel process for preparing antibacterial β-lactams i.e. penicillins and cephalosporins by the action of an acylase on a penicillin or cephalosporin nucleus amine as substrate and an ester (I) of the following formula as the acyl source:

(wherein
RCO is an acyl group in penicillin or cephalosporin side chains;
X is a hydrogen atom, lower alkyl group or hydroxy-lower alkyl group;
Y is a hydrogen atom or a lower alkyl group; and n is a positive integer)

The reaction for the synthesis proceeds in a homogeneous solution and is suitable for efficient continuous production. This overcomes previous troubles preventing commercial acylation for production of penicillins and cephalosporins by the action of an acylase.

Processes are well known for preparing penicillins or cephalosporins by reacting a methyl or ethyl ester of an acid having acyl moiety to be introduced with 6-aminopenicillanic acid or 7-aminocephalosporanic acid or reactive derivatives thereof (e.g. Japanese Patent Application Publication No. 47-25388, 47-29588, 48-26985, 48-35090, 48-99393, 49-14687, 49-36890, 49-48892, 49-75787, 49-134893 and 52-110896). It is to be noted that the acyl source of above references are invariably a lower alkyl ester, especially methyl ester.

The present inventors observed during similar reactions that many lower alkyl esters are sparingly soluble in water and attain only low concentration insufficient for effective acylation.

As a result, known synthesis with immobilized enzyme often has difficulty due to two-phase formation or plug formation in a column to prevent smooth elution.

To solve these problems, many esters are made and tried on substrates for the acylases to find (poly)ethylene glycol ester and the like very suitable. These esters are freely miscible with water and do not form plugs in a column upon acylation. Therefore they can be effectively used in continuous reactions with a column of immobilized enzyme. Thus, the molar ratio of acyl source and amino source could be reduced, yield could be improved, concentration of substrates and products could be elevated, unreacted starting material and products could be collected from a reaction mixture efficiently and other merits have been discovered for enzymatic synthesis.

Thus, this invention is a novel enzymatic synthesis of β-lactam antibacterials by reacting an ester of the formula (I) with aminoazetidinone carboxylic acid of the formula (II) in the presence of acylase in an aqueous medium to produce a β-lactam antibacterial of the formula (III):

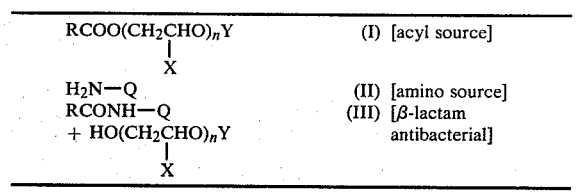

[wherein
RCO— is an acyl group;
X— is a hydrogen atom, lower alkyl group or hydroxy-lower alkyl group;
Y— is a hydrogen atom or a lower alkyl group;
n is a positive integer; and
Q— is a group of the formula:

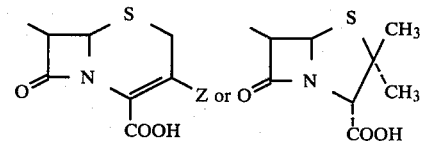

(in which Z is a hydrogen or halogen atom, a nucleophilic group, a methyl, halomethyl or methyl substituted by a nucleophilic group)]

As will be explained later, enzymes of bacterial or fungal origin are especially important as acylase for this invention from the view point of e.g. production, efficiency, cost and stability.

Especially suitable bacteria include acylase-producing bacteria belonging e.g. to genus Micrococcus, Arthrobacter or Bacillus, including specific strains of *Micrococcus roseus* M-1054-1 (FERM-P 3744), *Micrococcus luteus* M-331-1, *Arthrobacter globiformis* M-345-2 (FERM-P 3743), *Bacillus circulans* M-1123-5 (FERM-P 5153) and *Bacillus megaterium* NRRL B-5385.

The compounds of formula (I) are novel compounds indispensable as constituents of this invention and are highly water-soluble concomitantly susceptible as substrate of the acylases. They are useful acyl sources and are useful from this point of view.

In the above formula, the acyl group represented by RCO— is an acyl of natural or synthetic, penicillins or cephalosporins, which is susceptible as a substrate of the said amido-acylase in a form of the ester derivative (I).

Representative RCO— groups can be straight, branched, cyclic or partially cyclic lower alkanoyl or lower alkenoyl; monocyclic lower aralkanoyl, monocyclic aryloxylower alkanoyl, (O, N or S)-heterocyclic-lower alkanoyl, (O, N or S)-heterocyclic thio-lower alkanoyl, cyanoacetyl, cyanomethylthioacetyl, monocyclic arylglycyl, monocyclic cycloalkenylglycyl, monocyclic arylglycolyl, N-acyl-arylglycyl, monocyclic arylmalonyl or arylsulfoalkanoyl, all above optionally having lower alkyl, aminomethyl, halogen, hydroxy, lower alkanoyloxy or lower alkoxy as a substituent, and preferably containing 1 to 15 carbon atoms.

Said ester (I) has as an alcoholic moiety containing n units of an ethyleneglycol unit of the formula —(CH₂CHXO)— as a constituent. Said number n is usually from 1 to 20, especially from 4 to 15. Another end Y of the ethyleneglycol chain can be a hydrogen or in the form of a lower alkyl ether. It has been found that enzymatic activity for the acyl source is not greatly affected by the ethyleneglycol chain length. As a result, the ester (I) used as acyl source can be a mixture of several esters having various n values to obtain equivalent effects.

These esters can be prepared by a conventional method e.g. by the reactions of an acid RCOOH with glycerin or (poly)ethyleneglycol or ethylene oxide, by dehydration, condensation, or through acid halide, or chemically reactive esters of another type for ester exchange reaction.

The aminoazetidinone carboxylic acid (II) is a penicillin nucleus amine or cephalosporin nucleus amine capable of being used as a substrate of the acylase applicable in a form of water soluble salt or ester.

In the formula (II), Q is penicillin or cephalosporin nucleus represented by the following partial formula:

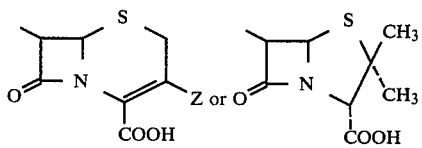

(wherein Z is as defined above).

Said group Z is a substituent at the 3-position of cephalosporin antibacterials i.e. hydrogen or halogen atom, or nucleophilic group or methyl optionally substituted by said nucleophilic group. Such nucleophilic group has been disclosed in e.g. Japanese Patent Application Publication No. 49-81381.

Representative Z groups may have up to 7 carbon atoms including hydrogen, halogen, lower alkoxy, monocyclic (O, N or S)-heterocyclic thio, lower alkyl, monocyclic lower aralkyl, lower alkanoyloxy, lower alkanoyloxy-lower alkyl, monocyclic (O, N or S)-heterocyclic thio-lower alkyl and pyridinium-lower alkyl. These can be substituted by lower alkyl, carboxy-lower alkyl, lower alkoxy, carbamoyl or halogen. A heterocycle in RCO or Z has 1 to 4 heteroatoms.

An aminoazetidinone carboxylic acid (II) can be used in a form of enzymatically acceptable water-soluble salts (e.g. sodium salt, potassium salt, calcium salt) or water-soluble ester (e.g. methanesulfonylethyl ester, acetonyl ester, lower alkoxy-lower alkyl ester), or it may be used in a form of water-soluble acid addition salt (e.g. mineral acid salt, carboxylic acid salt or sulfonic acid salt) as an equivalent starting material. It is a known compound or closely related compound which can be produced from known substance with a known a method.

The enzyme for this invention can be an acylase of plant, animal, fungal or bacterial origin. Among them, the most suitable industrially are fungal or bacterial enzyme from the view-point of availability. The enzyme can be stored for a long time, used repeatedly and available at a concentration higher than the MIC of the original bacteria.

Representative bacteria or fungi for the acylase source include strains of microorganisms belonging to e.g. genera Acetobacter, Achromobacter, Aeromonas, Alkaligenes, Arthrobacter, Blevibacterium, Beneckea, Bacillus, Corynebacterium, Escherichia, Flavobacterium, Gluconobacter, Kluyvera, Microbacterium, Micrococcus, Nocardia, Proteus, Pseudomonas, Rhodopseudomonas, Spilirum, Staphylococcus, Xanthomonas, Aphanocladium or Cephalosporium, or natural or artificial mutants or variants thereof capable of producing acylase for the condensation of this invention. Such strains include those described in e.g. Advances in Applied Microbiology, Volume 20, page 217 (1976) or natural or artificial mutants thereof available in the reaction of this invention.

DETAILED DESCRIPTION

Especially preferable bacteria for enzyme origin for this invention include the following three strains.
1. *Micrococcus roseus* M-1054-1, FERM-P 3744, ATCC 31251
2. *Arthrobacter globiformis* M-345-2, FERM-P 3743, ATCC 31250.
3. *Bacillus circulans* M-1123-5, FERM Acceptance No. 5153.

The above strains have the following characteristics:

Micrococcus roseus M-1054-1

(1) Morphological characteristics (meat extract agar slant, 28° C., 24 hours)

Cocci (diameter 1.0–1.2μ) links in single or double strands. Motility is not observed and no spores are formed. Gram stain is positive after incubation for 24 hours. Acid-fast strain is negative.

(2) Characteristics on various media
a. Meat extract agar plate culture (28° C., 2 days) Pinkish circular colonies with shining surface are formed. They are entire, convex and opaque colonies with butyrous structure. No soluble pigment is observed.
b. Meat extract agar slant culture (28° C., 1 day) Moderate pinkish and filamentous growth is observed. The colonies are convex and opaque wih a shining surface. No soluble pigment is observed.
c. Meat extract liquid culture (28° C., 2 days) Filamentous growth is observed on the surface with homogeneous turbidity and some precipitation.
d. Meat extract gelatin stub culture (24° C. 30 days) Growth is observed on the surface but no gelatin liquefaction.
e. Litmus milk culture (28° C., 7 days) A little decolorization occurs at neutral pH and coagulation and peptonization of milk are not observed.

(3) Physiological characteristics

| | |
|---|---|
| Reduction of nitrate | + |
| Denitrification | − |
| MR test | − |
| VP test | − |
| Indole formation | − |
| Hydrogen sulfide formation | − |
| Starch hydrolysis | + (weak) |
| Utilization of citric acid | + |
| Utilization of ammonium salt | + |
| Pigment formation | Water insoluble, pale yellow |
| Urease | + |
| Oxidase | + (weak) |
| Catalase | + |
| Ammonia formation from arginine | − |
| Acid formation from glucose (I.C.S.B. method) | |
| Oxidative | − |
| Fermentative | − |
| Oxygen requirement | Aerobic |
| O-F test | Oxidative |

PH for growth 6.1−, 7.0+, 7.9+, 8.8+, 9.8+
Temperature for growth 4° C.−, 10° C.−, 20° C.+, 28° C.++, 37° C.+, 42° C. −

Sugar utilization

Sugar accompanying acid formation: L-arabinose, D-glucose, D-fructose.

Sugar not accompanying acid formation: D-xylose, D-mannose, D-galactose, maltose, sucrose, lactose, D-trehalose, D-sorbitol, D-mannitol, inositol, glycerol, starch.

(Neither sugar results in gas formation.)

From these characteristics, it is concluded that the above microbe belongs to *Micrococcus roseus* and is a new strain because of no liquefaction of gelatin, weak hydrolysis of starch and no growth at a temperature below 10° C.

Arthrobacter globiformis M-345-2

(1) Morphological characteristics (meat extract agar slant, 28° C., 24 hours)

Rods (0.7–1.0×1.5–3.0μ) links in single or double strands to form a letter V and sometimes linkage is recognized. Motility and spores are not observed. Gram stain is positive after incubation for 6, 18 and 24 hours. Acid-fast stain is negative. Cells turn to cocci (diameter 0.7–1.2μ) after incubation for 3 days on meat extract agar slant medium and return to rods by incubation for several hours in meat extract liquid medium.

(2) Characteristics on various media
   a. Meat agar plate culture (28° C., 2 days) Pale yellowish circular colonies with a shining surface are formed. They are entire, convex and opaque colonies having butyrous structure. No soluble pigment is observed.
   b. Meat extract agar slant culture (28° C., 1 day) Moderate, yellowish and filamentous growth is observed. The colonies are convex and opaque with a shining surface. No soluble pigment is observed.
   c. Meat extract liquid culture (28° C., 2 days) Homogenous turbidity but no growth is observed with some precipitation.
   d. Meat extract gelatin stub culture (24° C., 30 days) Growth on surface is observed but no gelatin liquefaction.
   e. Litmus milk culture (28° C., 7 days) Decolorization at alkaline pH and no coagulation are observed with gradual peptonization.

(3) Physiological characteristics

| | |
|---|---|
| Reduction of nitrate | + |
| Denitrification | − |
| MR test | − |
| VP test | − |
| Indole formation | − |
| Hydrogen sulfide formation | + |
| Starch hydrolysis | − |
| Ultilization of citric acid | + |
| Utilization of ammonium salt | + |
| Pigment formation | − |
| Urease | + |
| Oxidase | + (weak) |
| Catalase | + |
| Cell-wall amino acid | Glutamic acid, alanine and lysine. |
| Nutrient requirement | Thiamine (The growth is stimulated with amino acids.) |
| Oxygen requirement | Aerobic |
| O-F test | Oxidative |

PH for growth 6.1−, 7.0+, 7.9++, 8.8+, 9.8+.

Temperature for growth 4° C.−, 10° C.+, 20° C.++, 28° C.++, 37° C.++, 42° C.−.

Sugar utilization

Sugar accompanying acid formation: D-fructose Sugar not accompanying acid formation: L-arabinose, D-xylose, D-glucose, D-mannose, D-galactose, maltose, sucrose, lactose, D-trehalose, D-sorbitol, D-mannitol, inositol, glycerol, starch.

(Neither sugar results in gas formation.)

These characteristics are directly compared with *Arthrobacter globiformis* ATCC 8010 and it is concluded that the above strain M-345-2 is distinguished in positivity of Gram-stain at early stage of incubation (28° C., 6 hours) and thiamine requirement as a growth factor. Besides, they are different in starch hydrolysis and reduction of nitrate. However, the differences are merely noted since they can not be recognized as remarkable differences between strains. From the above fact, it is concluded that the above strain is a new thiamine-requirement mutant of *Arthrobacter globiformis* ATCC 8010.

Bacillus circulans M-1123-5

(1) Morphological characteristics (Meat extract agar slant, 28° C., 24 hours)

Rods (0.8–1.0×2.0–4.5μ) link in single or double strands. No motility is observed and Gram-stain is positive after incubation for 24 hours. Acid-fast stain is negative.

Spores are formed on soybean agar slant culture after incubation at 28° C. for 4 days. Spores are 0.8–1.0×1.5×2.0μ in size and are cylindrical in shape. They are positioned on central or slightly at end. Sporangium is swollen. Stain of spores is positive.

(2) Characteristics on various media
   a. Meat agar plate culture (28° C., 2 days) Cream-colored circular colonies with a shining surface are formed having entire, convex, opaque and butyrous structure. No soluble pigment is observed.
   b. Meat extract agar medium (28° C., 1 day) Moderate, cream-colored and filamentous growth is observed. Colonies are opaque with shining surface.
   c. Meat extract liquid culture (28° C., 2 days) No growth on surface but homogenous turbidity is observed.
   d. Meat extract gelatine stub culture (24° C., 30 days) Growth on surface which extends into the inside is observed. Liquefaction proceeds gradually after incubation for 10 days.
   e. Litmus milk culture (28° C., 7 days) No change occurs at neutral pH and acidification begins on about the 22nd day with gradual coagulation.
   f. Sabouraud-dextrose agar slant culture (28° C., 2 days) Little growth is observed.
   g. Soybean agar slant culture (28° C., 2 days) Moderate growth is observed.
   h. Tyrosine agar plate culture (28° C.) Moderate growth is observed. The medium does not turn brown.

(3) Physiological characteristics

| | |
|---|---|
| Reduction of nitrate | + |
| Denitrification | + |
| MR test | − |
| VP test | − |
| Indole formation | − |
| Hydrogen sulfide formation | + |
| Starch hydrolysis | + |

| -continued | | |
|---|---|---|
| Utilization of citric acid | | + |
| Utilization of ammonium salt | | + |
| Pigment formation | | − |
| Urease | | + |
| Oxidase | | + |
| Catalase | | + |
| Deamination of phenylalanine | | − |
| pH of VP broth | | 6.1 |
| Lecitinase | | − |
| Oxygen requirement | | Facultative anaerobic |
| O-F test | Oxidative | + |
| | Fermentative | + | pH for growth 5.2−, 6.1+, 7.0+, 7.9++, 8.8+, 9.8−.
Salt concentration for growth 0.5%+, 3%+, 5%+, 7%−.
Temperature for growth 4° C.−, 10° C.−, 20° C.+, 28° C.++, 37° C.++, 42° C.+, 52° C.−.
Sugar utilization
Sugar accompanying acid formation: L-arabinose, D-mannose, D-glucose, D-fructose, maltose, sucrose, lactose, D-trehalose, D-mannitol, glycerol, starch
Sugar not accompanying acid formation: D-xylose, D-galactose, D-sorbitol, inositol.
(Neither sugar results in gas formation)

From the above result, it is concluded that the above microbe is a strain described in Bergy's Manual of Determinative Bacteriology, 8th edition, page 539 (1974).

These fungi or bacteria can be used in the form of cells, crushed cells, crude enzyme, pure enzyme, immobilized enzyme or a like preparation available for the said acylase.

The cells are produced usually under aerobic condition e.g. by liquid propagation with aeration. The propagation medium is an aqueous solution at pH 6 to 8 containing e.g. peptone, meat extract, yeast extract, soy bean protein hydrolyzate, soy bean extract or corn steep liquor as nitrogen source; syrup, glucose or glycerin as carbon source; phosphate, magnesium salt or sodium chloride as inorganic salt; and if required in the presence of a suitable amount of growth promoting factor. Propagation is carried out at 20° to 40° C. for 10 to 60 hours. The cells thus prepared can be separated by e.g. filtration or centrifugation, and washed with e.g. water, acetone, methanol or ethanol.

When an acylase produced by a microorganism is excreted outside the cells and is accumulated in the fermentation broth, the acylase is collected by addition of an adsorbent to the broth from which cells have been removed by e.g. filtration, centrifugation, or by salting out with e.g. ammonium sulfate or sodium chloride, or by precipitating by the addition of a water-miscible organic solvent e.g. methanol, ethanol or acetone, or by a similar method to separate the enzyme and, if required, purified by dialysis, absorption, reprecipitation, gel filtration, chromatography or by lyophillization. Cell-free broth may be used as the acylase source.

In the case of an intracellular enzyme, wet cells, dry cells or the like may be used as enzymes, or they may be broken with ultrasonic wave or mechanical means and, if required, mixed with a detergent to separate the portion having acylase activity from the cell-body.

In industrial use, the acylase can be bound by e.g. absorption or chemical binding on a carrier e.g. alumina, diatomaceous earth, Celite, acid bentonite, active clay, kaolin, calcium phosphate, hydroxyapatite, fibre, cellulose, agar, ion-exchange resin, synthetic resins, glass beads, sepharose, sephadex, or agarose to produce immobilized enzyme.

When an acylase produced by a microorganism is used as an absorbed enzyme, the separated enzyme in water or fermented broth is mixed with an adsorbent e.g. celite, dicalite, calcium phosphate gel, active clay, acid bentonite or high porous synthetic polymer to absorb the acylase and the product is filtered and washed with water and used as the enzyme source.

Further, instead of methacrylate copolymer, acrylate copolymer, maleate copolymer, carboxystyrene copolymer, sulfostyrene copolymer, carboxymethyl cellulose or ion exchange resins may be used in a free acid or salt form to produce ion-bound immobilized enzyme.

Immobilized enzyme by a chemical bonding is prepared by conventional method e.g. that described in Methods in Enzymology, Volume 44, page 25 (1976) including the cyanogen halide method, oxiran method, divinylsulfonic acid method, haloacetyl halide method, disulfide method, aldehyde-nitrile method, phenylenediamine-cyclohexylisocyanide method or γ-ray irradiation method.

When the cell body is used as the acylase, the cell is immobilized in e.g. polyacrylamide resin by a conventional process to make inclusion immobilized enzyme.

By using the above-disclosed methods, the following compounds can be successfully prepared: cefaclor, cefacetrile, cefazolin, cefatrizin, cefadroxyl, cefapyrin, cefamandole, cefalexin, cefaloglycin, cefalotin, cefaloridine, cefaclomezin, cefsulodin, ceftezol, cefradin, CGP-9000, phenylacetamidocephalosporanic acid, phenoxyacetamidocephalosporanic acid, amoxicillin, ampicillin, carbenicillin, phenoxymethylpenicillin, phenoxypropylpenicillin and benzylpenicillin.

The process of this invention is carried out by contacting an acylase with the said ester (I) and the aminoazetidinone carboxylic acid (II) in water preferably at 20° C. to 40° C.

Usually, the concentration of the aminoazetidinone carboxylic acid (II) is 0.1 to 50 mg/ml, preferably 5 to 20 mg/ml, molar concentration of ester (I) is 1 to 10 times, preferably 2 to 5 times, as that of said carboxylic acid (II).

The concentration of carboxylic acid (II) can be lower than 5 mg/ml resulting an efficient reaction. In some cases the objective compound (III) can be obtained in over 90% yield. The conversion rate varies depending on the reaction condition, especially on enzymatic activity used per unit amount of the starting material. Usually, the reaction is carried out at 35° to 40° C. at pH 6 to 8.

The acylase is contacted with said starting materials (I) and (II) by adding an aqueous solution of the crude or purified enzyme into the reaction mixture, if desired.

Bacteria or fungi producing intracellular or extracellular effective acylase can be used as a cell suspension in water or broth medium by adding it into the reaction medium to use as the enzyme source.

Said immobilized enzyme can be used as an enzyme source by batch or column method or by a conventional method.

Reaction time in the batch method, flow rate and reaction temperature in the column method can be determined by observing the yield of the product or disappearance of the starting materials. The reaction mixture is filtered to remove solid material, washed with an organic solvent to remove neutral substances e.g. ester (I), and by a conventional method e.g. fractional extraction, fractional absorption, recrystallization or chromatography, to obtain the objective material (III).

This invention takes the novel (poly)ethyleneglycol ester (I) as the acyl source, freely miscible with water and carried out in a homogeneous phase, to avoid plug formation in the case of a column method efficiently. This is indeed a remarkable improvement as compared to known acyl sources, methyl esters with a low solubility (cf. only 1% concentration of 2-thienylacetic acid methyl ester can dissolve in water) to result in a plug formation to inhibit smooth flow. In the case of known methyl esters, a high concentration of substrate blocks the enzyme reaction. However, this invention using the water soluble ester (I) gives the objective material in a good yield even in such higher concentration. Further, this invention, an enzymatic synthesis, allows at higher concentration of the substrate or product an efficient recovery of starting material or objective product from the reaction mixture.

As stated above, this invention is a very valuable enzymatic synthesis of β-lactam antibacterials from an industrial point of view.

The following examples are given to show detailed embodiments of this invention.

EXAMPLE 1

(*Bacillus circulans* M-1123-5) (Crude enzyme)

An aqueous medium containing soluble starch (0.5%), polypeptone (0.5%) and corn steep liquor (0.5%) is adjusted to pH 7.0 and inoculated with *Bacillus circulans* M-1123-5. After preincubation at 32° C. for 24 hours, the broth is transferred to the same aqueous medium (100 times volumes) as described above. The mixture is shaken for 42 hours at 32° C. The obtained broth is centrifuged at 6500 rpm to remove cells. Separated supernatant (5 liters; pH 7.7) is adjusted to pH 7 with hydrochloric acid, mixed with ammonium sulfate to get 70% saturation and centrifuged. The precipitate is dissolved in deionized water (110 ml) and desalted by dialysis with deionized water (14 liters). Dialyzed solution is centrifuged to remove insoluble contaminant. The supernatant (227 ml) is lyophilized to obtain crude enzyme (1.65 g).

(Binding ability of various carriers)

A given amount of a carrier on Table I is suspended in water and mixed with 10% aqueous cyanogen bromide while keeping the pH at 11 by adding aqueous 4 N-sodium hydroxide. The mixture is stirred for 10 minutes at 20° C. filtered and washed with cold water and M/30-phosphate buffer (pH 8) to obtain activated carrier.

The activated carrier is added to an aqueous solution of the crude enzyme and kept at 4° C. overnight. The produced immobilized enzyme is collected by filtration, washed thoroughly with M/30-phosphate buffer and stored at room temperature.

(Acylating capacity determination by batch process)

To a solution of 7-aminocephalosporanic acid (hereinafter called 7-ACA) (15 mg), 2-thienylacetic acid tetraethyleneglycol ester (hereinafter called TA-tetra) (75 mg) in M/20-phosphate buffer (5 ml) is added an immobilized enzyme prepared above. The mixture is shaken at 37° C. for 40 minutes. Produced cephalothin is determined by assaying antibacterial activity to *Bacillus subtilis* PCI-219.

(Acylating capacity determination by column process)

A mixed solution composed of 7-ACA (5 mg/ml), TA-tetra (25 mg/ml) and M/20-phosphate buffer (pH 7.0) is passed through a column of the immobilized enzyme at 37° C. at a flow rate of 25 ml/hr. Produced CET in the eluate is estimated by antibacterial assay against *Bacillus subtilis* PCI-219 to calculate the conversion rate.

The obtained data are given on Table I.

(Reactivity of TA-esters)

1. Batch method.

TABLE 1

| | Preparation and activity of immobilized enzyme | | | | | |
|---|---|---|---|---|---|---|
| | Carrier | | | | | |
| Condition | Sephadex G | Avicel | Cellulose powder | Agar Gel | Agar powder | Sepharose |
| Immobilized enzyme | | | | | | |
| Carrier | 10ml | 1 g | 1 g | 10ml | 1 g | 20ml |
| Suspension (ml) | 10 | 10 | 10 | 10 | 20 | 40 |
| 10% BrCN aq. (ml) | 30 | 30 | 30 | 30 | 30 | 60 |
| Crude enzyme aq.soln. (ml) | 18 | 18 | 18 | 18 | 16 | 36 |
| Bound Protein ratio (%) | 89.1 | 52.3 | 25.3 | 26.3 | 82.2 | 87.5 |
| Wet Bound Protein (g) | 4 | 3.2 | 4 | 8.3 | 12.5 | 21 |
| Batch Process | | | | | | |
| Wet Immobilized enzyme (mg) | 111 | 89 | 61 | 230 | 390 | 290 |
| 7-ACA→CET Conversion rate (%) | 85 | 62 | 4 | 92 | 67 | 101 |
| Column Process | | | | | | |
| Wet Immobilized enzyme (ml) | — | — | — | 11 | — | 13 |
| 7-ACA→CET Conversion rate (%) | — | — | — | 75.2 | — | 87.6 |

To a solution of 7-ACA (30 mg) and TA-esters (given amount) in M/10-phosphate buffer (pH 7.0) (10 ml) is added an immobilized enzyme (0.9 g) on Sepharose 4B, and the mixture is stirred at 37° C. for 3 hours. Concentration of CET in the reaction mixture is estimated by assaying antibacterial activity against *Bacillus subtilis* PCI-219 and conversion rate from 7-ACA to CET is calculated. The result is listed on Table 2.

2. Column method.

A solution of 7-ACA (5 mg/ml) and TA-ester of the following Table in M/20-phosphate buffer is passed through a column of immobilized enzyme (12 ml) at 37° C. at a flow rate of 25 ml/hr. Concentration of CET in the eluate is determined by assaying antibacterial activity against *Bacillus subtilis* PCI-219 to estimate the yield on Table 3 in the laminar flow state. (Immobilization of purified enzyme)

Into an aqueous medium (pH 7.0) containing soluble starch (0.5%), peptone (0.5%) and corn steep liquor (0.5%) is inoculated *Bacillus circulans* M-1123-5 and shaken for 24 hours at 32° C. Prepared preincubate is added into 100 times by volume of aqueous medium of the same composition as above and shaken at 32° C. for 2 days.

TABLE 2
Reactivity of TA esters by batch process

| Esters | Initial amount (mg/ml) | Conversion rate (%) |
|---|---|---|
| TA-tetraester[1] | 15.0 | 77.1 |
| TA-pentaester[2] | 10.2 | 80.6 |
| TA-octaester[3] | 17.7 | 76.2 |
| TA-tetraester methyl ether[4] | 15.7 | 73.3 |
| TA-octaester methyl ether[5] | 24.0 | 68.2 |
| TA-glycerin ester[6] | 23.3 | 73.7 |

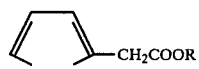—$CH_2COOR$

[1] $R = -(CH_2CH_2O)_4H$
[2] $R = -(CH_2CH_2O)_5H$
[3] $R = -(CH_2CH_2O)_8H$
[4] $R = -(CH_2CH_2O)_4CH_3$
[5] $R = -(CH_2CH_2O)_8CH_3$
[6] $R = -CH_2CHOHCH_2OH$

TABLE 3
Reactivity of TA esters by column method

| TA-esters | | 7-ACA→CET Conversion rate (%) | |
|---|---|---|---|
| Type | mg/ml | Sepharose 4B | Agar gel |
| TA-tetraester[1] | 25.0 | 87.6 | 85.0 |
| TA-pentaester[2] | 17.0 | 69.9 | — |
| TA-tetraester methyl ether[4] | 29.6 | 86.5 | 86.5 |
| TA-octaester methyl ether[5] | 26.1 | 69.8 | 69.8 |
| TA-glycerin ester[6] | 55.0 | 82.0 | — |

TABLE 4
Acylating capacity of immobilized pure enzyme

| Elute (ml) | 39 | 173 | 306 | 405 | 731 | 782 | 917 | 1089 | 1156 | 1294 | 1432 | 1534 |
|---|---|---|---|---|---|---|---|---|---|---|---|---|
| 7-ACA→CET Conversion rate (%) | 84.8 | 85.2 | 85.3 | 90.4 | 85.7 | 86.3 | 88.5 | 86.9 | 86.6 | 82.5 | 83.1 | 82.0 |

The broth is centrifuged to remove cells, diluted with aqueous 70% ammonium sulfate to salt out the protein fraction. The fraction is dialyzed to remove salts and lyophilized to give crude enzyme. The crude enzyme thus obtained (1.1 g) is dissolved in M/100-phosphate buffer (pH 8.0) (200 ml) and chromatographed through a column of DEAE-cellulose (Whatman-DE 52; 24 mm$\phi \times$160 mm: 73 ml) by the gradient elution of an aqueous sodium chloride solution (from 0 to 0.6 M). Active fractions are collected, concentrated with Collodion Bag SM-13200 (product of Zartorius Co.) and dialyzed to give a purified aqueous enzyme solution (35 ml). To this solution is added 4% agar gel (beads form) (20 ml) activated with cyanogen bromide, and the mixture is stirred overnight to react forming immobilized enzyme. The product is washed thoroughly with M/30-phosphate buffer (pH 7.0) containing 0.5 M-sodium chloride to obtain immobilized enzyme.

Through a column of this solid enzyme (14.1 ml) filled in 10 mm$\phi$ column is passed a M/20-phosphate buffer solution (pH 7.0) containing 7-ACA (10 mg/ml) and TA-octaester methyl ether[5] (142.2 mg/ml) at 37° C. at a flow rate of 16 ml/hr. Elute volume and 7-ACA→CET conversion rate are as shown on the following Table 4. Within the range observed, the conversion rate remained on the same level to show nearly constant enzyme activity.

The eluate contains, further to objective CET, TA-tetraester methyl ether and 2-thienylacetic acid each recoverable in yields of 90 to 95%, 60 to 85% and 8 to 10% of the substances in the eluate.

(Absorbed enzyme)

In an aqueous medium (pH 7.0) containing soluble starch (0.5%), peptone (0.5%) and corn steep liquor (0.5%) is inoculated *Bacillus circulans* M-1123-5 and preincubated at 32° C. for 24 hours. The preincubate (1 part) is added to an aqueous medium (100 parts) of the same composition, and the mixture is propagated at 32° C. for 24 hours. The broth is centrifuged to remove cells, adjusted pH to 7.0 by adding aqueous 1 N-sodium hydroxide, mixed with 1/50 weight of Celite 560 (distributed by Johns-Manville Sales Co.), stirred at 0° to 4° C. for 40 minutes and filtered. The solid fraction is washed with M/20-phosphate buffer to obtain immobilized absorbed enzyme.

Through a column of this absorbed enzyme (4 g) filled in 10 mm $\phi$ tube is passed a solution of 7-ACA (5 mg/ml and TA-tetra ester in M/20-phosphate buffer at 37° C. at a flow rate of 25 ml/hr. During passage of 75 ml of the solution, CET product formed is estimated by assaying antibacterial activity against *Bacillus subtilis*, PCI-219. The results are given on Table 5 in terms of conversion rate (%) from 7-ACA.

TABLE 5
Acylating capacity of absorbed enzyme on Celite 560

| | | TA-tetraester (mg/ml) | | | | |
|---|---|---|---|---|---|---|
| | | 25 | 25 | 25 | 18.8 | 12.5 |
| pH | | 6.0 | 7.0 | 8.0 | 7.0 | 7.0 |
| 7-ACA→CET Conversion rate (%) | In eluate | 62.8 | 72.9 | 71.6 | 63.0 | 63.0 |
| | Isolated Na salt | 48.5 | 67.2 | 49.3 | 64.2 | 53.0 |

(Isolation of the product from the reaction mixture)

A reaction mixture is first extracted three times with the same volume of ethyl acetate each time to recover TA-esters in the extract solution. The remaining aqueous layer is acidified to pH 3.6, washed with ether, adjusted to pH 2.0 and extracted with ethyl acetate. The aqueous layer contains 7-ACA. The second extract solution is washed with saturated saline, dried over sodium sulfate and concentrated in vacuo. The concentration ethyl acetate solution is mixed with sodium 2-ethylhexanoate (ca. 1.5 mole equivalents), allowed to stand at 4° C. for 24 hours and filtered to collect CET sodium.

By this method, one can recover about 80 to 95% of CET in the reaction mixture.

(Selectivity of the acylases)

(Immobilized enzyme)

According to above methods, *Bacillus circulans* M-1123-5, *Arthrobacter globiformis* M-345-2 or *Arthrobacter flagerum* M-2183-1 is cultured and filtered to a cell free culture broth. The broth is treated with sodium chloride to salt out the enzymatic fraction, which is collected, dialyzed and chromatographed over a DEAE-cellulose column to obtain a partially purified enzyme. The purified enzyme is treated with 4% agar gel activated with cyanogen bromide.

(Reaction solution)

To a solution of an ester (I) (45 mg) and aminoazetidinone carboxylic acid (II) (9 mg) in M/20-phosphate buffer (pH 6 to 7) (3.0 ml) is added immobilized enzyme (0.15 to 0.5 g) and stirred at 37° C. for 3 hours 45 minutes. After the reaction, the mixture is filtered through a cotton plug, and the obtained filtrate is checked by a thin-layer chromatogram and paper-disc assay method using *Bacillus subtilis* PCI-219 as a test microorganism to detect and determine each product. The results are listed on Table 6.

EXAMPLE 2

(*Arthrobacter globiformis* M-345-2)

(Immobilized enzyme)

Into an aqueous medium (pH 7.0) containing glucose (0.5%), peptone (0.5%) and corn steep liquor (0.5%) is inoculated *Arthrobacter globiformis* M-345-2 which is preincubated at 28° C. for 24 hours. Then, the broth is added to 100 volumes of an aqueous medium having the same composition and propagated at 28° C. for 2 days.

TABLE 6

$$RCOO(CH_2CHO)_nY$$
$$|$$
$$X$$

$$H_2N-Q \longrightarrow RCONH-Q$$

| R | Y n | Q | R f* | B. Circulans M-1123-5 | A. globiformis M-345-2 | A. fragerum M-2183-1 |
|---|---|---|---|---|---|---|
| thiophene-CH₂— | H 4 | azetidinone-CH₂OCCH₃ with COOH | 0.7 | 49.6 | 23.2 | 28.5 |
| thiophene-CH₂— | H 4 | azetidinone-CH₃ with COOH | 0.72 | 36.1 | 16.5 | 5.6 |
| thiophene-CH₂— | H 4 | azetidinone-H with COOH | 0.54 | 6.0 | — | — |
| thiophene-CH₂— | H 4 | azetidinone-S-thiadiazole-CH₃ with COOH | 0.63 | 40.2 | 25.1 | 23.0 |
| phenyl-CH₂— | H 4 | azetidinone-CH₂OCCH₃ with COOH | 0.71 | 36.2 | 10.1 | 16.1 |
| phenyl-CH₂— | H 4 | azetidinone-(CH₃)(CH₃) with COOH | 0.71 | Decomposition with penicillinase | 18.0 | 20.3 |

TABLE 6-continued $$RCOO(CH_2\overset{\underset{\displaystyle |}{X}}{C}HO)_nY$$

$$H_2N-Q \longrightarrow RCONH-Q$$

| R | Y n | Q | R f* | B. Circulans M-1123-5 | A. globiformis M-345-2 | A. fragerum M-2183-1 |
|---|-----|---|------|-----------------------|------------------------|----------------------|
| C₆H₅—OCH₂— | H 4 | 3-methyl cephem (S, CH₃, COOH) | 0.71 | + | + | — |
| C₆H₅—OCH₂— | H 4 | gem-dimethyl penam (S, C(CH₃)₂, COOH) | 0.71 | Decomposition with penicillinase | 21.0 | 80.2 |
| triazolyl-CH₂— (N=N / N-N-CH₂—) | CH₃ 5 | cephem with CH₂-S-thiadiazolyl-CH₃ | 0.5 | 55.7 | 43.7 | 54.9 |
| C₆H₅—CH(NH₂)— | CH₃ 2 | 3-methyl cephem | 0.13 | 29.6 | 10.6 | — |

*SiO₂ plate/acetone:acetic acid:water (95:5:10V/V)

After removing mycellium by centrifugation, the broth (530 ml) is mixed with aqueous 70% ammonium sulfate to salt out a precipitate, which is purified by column chromatography over DEAE cellulose, concentrated with collodion bag and dialyzed to give a purified enzyme solution (24 ml). To this solution (19 ml) is added 4% agar gel (10 ml) or Sepharose 4B (10 ml) each activated with 10% cyanogen bromide as in Example 1, and the mixture is reacted overnight. The product is collected by filtration and washed with water and M/30-phosphate buffer to give immobilized enzyme.

Through a column of this immobilized enzyme (10 ml) filled in 10 mm φ tube is passed at 37° C. a solution of 7-ACA (given amount) and TA-tetraester (120 mg/ml) in M/20-phosphate buffer (pH 7.0) at a flow rate of 25 ml/hr. The amount of CET in the eluate is estimated by antibacterial assay against Bacillus subtilis PCI-219 and listed on Table 7 in terms of conversion rate from 7-ACA to CET.

EXAMPLE 3

(Micrococcus luteus M-331-1)

(Mycelium)

Into an aqueous medium containing soluble starch (0.5%), peptone (0.5%) and corn steep liquor (0.5%) is inoculated Micrococcus luteus M-331-1, and the medium preincubated at 28° C. for 24 hours. The broth is added into an aqueous medium (100 volumes) of the same composition as above, and incubated for 3 days at 28° C.

TABLE 7

Acylating capacity of immobilized enzyme from Arthrobacter globiformis M-345-2

| 7-ACA | TA-ester | mg | Carrier | Conversion rate |
|-------|----------|-----|---------|-----------------|
| 1 mg/ml | TA-tetraester | 120 | Sephalose 4B | 83.7% |
| 2 | TA-tetraester | 120 | Sephalose 4B | 71.0 |
| 3 | TA-tetraester | 120 | Sephalose 4B | 56.3 |
| 1 | TA-tetraester | 114 | Sephalose 4B | 78.5 |
| 1 | TA-octaester methyl ether | 114 | Agar gel | 76.5 |
| 1 | TA-octaester methyl ether | 60 | Ager gel | 80.5 |

The broth is neutralized with hydrochloric acid to pH 7, centrifuged to collect the cells, washed with water and dried by washing with acetone to give 1.302 g of dry cells.

The dried cells (26 mg) are suspended in water (1.5 ml), diluted with a solution of 7-ACA (4 mg/ml) and TA-tetraester (20 mg/ml) in M/5-phosphate buffer (pH 7.0) (0.5 ml) and shaken for 3 hours at 37° C. to produce CET at a conversion rate of about 30%. (Immobilized cell entrapted in acrylamide gel)

In a solution of acrylamide monomer (750 mg) and N,N'-methylenebisacrylamide (40 mg) in M/20-phosphate buffer (pH 7.0) (4 ml) are suspended said dry cells (1 g). To this solution is added 5% 3-dimethylaminopropionitrile (0.5 ml) and aqueous 1% potassium persulfate (0.5 ml) and the mixture is allowed to stand at 25° C. for 30 minutes. Produced gel is crushed with blender and produced particles over 100 mesh are collected, filled in a 10 mm φ tube, and washed with M/20-phosphate buffer (pH 7.0) to give a column (10.2 ml) of immobilized cells.

Through this column is passed a solution of 7-ACA (1 mg/ml) and TA-tetraester (30 mg/ml or 6 mg/ml) in M/30-phosphate buffer (pH 7.0) at a flow rate of 25 mg/hr and CET amount in the eluate is estimated by assaying antibacterial activity against *Bacillus substilis* PCI-219 to obtain a conversion rate of 31.2 to 34.1% and 28.6 to 32.5%.

EXAMPLE 4

(*Xanthomonas axonopodis* M-621-1)

In an aqueous medium (pH 7.0) (100 ml) containing meat extract (1.0%), polypeptone (1.0%) and sodium chloride (0.5%) placed in 500 ml Sakaguchi flask is inoculated *Xanthomonas axonopodis* M-621-1 and shaken for 24 hours at 28° C. The broth is poured into a medium (700 ml) of the same composition in a 3-liter Mayer flask. After shaking at 28° C. for 41 hours, the broth is inoculated into six 30 L-jar fermenters each containing 15 liters of aqueous medium of the same composition. Propagation is continued for 2 days at 28° C. The broth is filtered to collect wet cells (1320 g). This is suspended in 0.1 M-phosphate buffer (pH 7.0) (8 liters), shreddered with Dynomil (product of Wiley A. Bahoffer Manufacturing Engineers Co.) to obtain an enzymatic extract solution. A part of this extract solution (2.4 liters) is treated with calcium phosphate and centrifuged to yield an active supernatant. The last is passed through Amberlite CG-50 (weakly acidic cation exchange resin) and equibrated with 0.01 M-phosphate buffer (pH 6.0) to trap the enzyme, which is eluted with 0.2 M-phosphate buffer containing 1 M-sodium chloride. The eluate is treated with Sepharose 4B (100 ml) activated with cyanogen bromide by a method similar to the preceding Examples. The binding ratio of the enzyme activity is 40%.

To a solution of D-phenylglycin diethyleneglycol ester methyl ether (45 mg) and 7-aminodeacetoxycephalosporanic acid (3 mg) is added the solid enzyme (0.15 g), and the mixture stirred at 37° C. for 3.5 hours. The reaction mixture is filtered through a cotton plug. Produced cephalexin in the filtrate is assayed by a paper disc method and the conversion rate from 7-aminocephalosporanic acid to cephalexin is calculated to obtain the value of 26.3%.

EXAMPLE 5

(*Micrococcus roseus* M-1054-1)

Into an aqueous medium (pH 7.0) (100 ml) containing glucose (0.5%), polypeptone (0.5%) and corn steep liquor (0.5%) is inoculated *Micrococcus roseus* M-1054-2, and the medium is shaken for 3 days at 28° C. The broth is adjusted to pH 7.0. The broth (4.5 ml) is added to a solution of 7-ACA (3%) and (i) 2-thienylacetic acid glycerin ester, (ii) 2-thienylacetic acid tetraethyleneglycol ester or (iii) 2-thienylacetic acid octaethyleneglycol ester in 0.2 M-phosphate buffer (0.5 ml) to react for 3.5 hours at 37° C. The reaction mixture is centrifuged to remove cells and the supernatant is assayed by paper disc assay method against *Bacillus subtilis* PCI-219 to the following values of produced cephalothin.
(i) 34 γ/ml,
(ii) 26 γ/ml and
(iii) 22 γ/ml.

EXAMPLE 6

The following are processes for synthesizing esters available for above enzymatic processes.

I. 2-Thienylacetic acid esters.

(1) Glycerin ester

A mixture of glycerin (9.2 g), 2-thienylacetic acid methyl ester (3.12 g) and potassium carbonate (0.1 g) is heated at 40° C. for 2 hours under reduced pressure while nitrogen is passed through a capillary tube. The reaction mixture is diluted with water (60 ml) and extracted with ethyl acetate (100 ml). The extract solution is dried over magnesium sulfate and concentrated to give 2-thienylacetic acid glycerin ester (3.55 g) as an oily material.
TLC: Rf=0.23 (Benzene-ethyl acetate (1:5)/$SiO_2$).
$n_D^{20}$=1.5405.
IR: $\nu_{max}^{film}$ 3400, 1740, 1175, 705 cm$^{-1}$.
Anal. Calcd. for $C_9H_{12}O_4S$: C 49.98; H 5.59; S 14.82.
Found: C 49.86; H 5.69; S 14.79.

(2) Pentaethyleneglycol ester methyl ether

A mixture of pentaethyleneglycol monomethyl ether (3.5 g), 2-thienylacetic acid methyl ester (1.32 g) and potassium carbonate (74 mg) is heated at 40° C. for about 2 hours under nitrogen atmosphere. The reaction mixture is purified by chromatography over silica gel to give 2-thienylacetic acid pentaethyleneglycol ester monomethyl ether as oil (4.6 g) from the fractions eluted with ethyl acetate.
TLC: Rf=0.22 (Benzene-ethyl acetate (1:5)/$SiO_2$).
$n_D^{20}$=1.4920.
IR: $\nu_{max}^{film}$ 1740, 1110, 705 cm$^{-1}$.
Anal. Calcd. for $C_{17}H_{28}O_7S$: C 54.23; H 7.49; S 8.51.
Found: C 54.38; H 7.35; S 8.74.

(3) Tetraethyleneglycol ester

To a solution of tetraethyleneglycol (40 g) in tetrahydrofuran (80 ml) and triethylamine (6.23 g) is dropwise added a solution of 2-thienylacetic acid chloride (bp. 112°-113° C./25 mmHg) (9.48 g) in tetrahydrofuran (20 ml) with stirring under ice cooling. After one hour of stirring, the mixture is filtered to remove separated solid material. The filtrate is concentrated at 40° C. under nitrogen atmosphere to obtain 48.6 g of residue. The residue is diluted with water (100 ml) to precipitate insoluble material. Supernatant is separated and extracted with ethyl acetate. The extract solution is concentrated under reduced pressure in a nitrogen stream to afford 2-thienylacetic acid tetraethyleneglycol ester (9.06 g). This does not contain ω,ω'-diester.
TLC: Rf=0.17 (Benzene-ethyl acetate (1:1)/$SiO_2$).
IR: $\nu_{max}^{film}$ 3440, 1735, 1120 cm$^{-1}$.
$n_D^{20}$=1.5080.
Anal. Calcd. for $C_{14}H_{22}O_6S$: C 52.81; H 6.96; S 10.07.
Found: C 52.62; H 7.06; S 10.09.
NMR: $\delta_{ppm}^{CDCl_3}$ 5.28brs1H, 3.86s2H, 3.63-4.36ml6H, 6.90-6.96m2H, 7.15-7.31m1H.

(4) Polyethyleneglycol ester monomethyl ether (part 1)

Polyethyleneglycol monomethyl ether (product of Nippon Yushi Kabushiki Kaisha with Trade name of Uniox M-210 having average molecular weight of 201) is heated at 2 mmHg to evaporate about one third. To the remaining liquid (15 g) are added 2-thienylacetic acid methyl ester (3.1 g) and potassium carbonate (51 mg), and heated at 80° C. under reduced pressure in a nitrogen atmosphere. After 3.5 hours, the content is purified by silica gel chromatography (70 to 230 mesh, 250 ml). The fractions are eluted with a mixture of benzene and ethyl acetate (1:1) and are concentrated to give 2-thienylacetic acid polyethyleneglycol ester monomethyl ether (n=4 to 13; mainly n=7, 8 and 9).

(5) Polyethyleneglycol ester monomethyl ether (part 2)

A mixture of polyethyleneglycol monomethyl ether (product of Nippon Yushi Kabushiki Kaisha with Trade name of Uniox M-400, average molecular weight 400) (40 g), 2-thienylacetic acid methyl ester (3.12 g) and potassium carbonate (0.123 g) is heated at 75° C. under reduced pressure in nitrogen atmosphere. After 3 hours, the reaction mixture is diluted with water (150 ml) and extracted with ethyl acetate. The extract solution is dried over sodium sulfate, concentrated in vacuo and chromatographed over silica gel (40 times volume). The fractions eluted with a mixture of acetonitrile and water (95:5) are collected and concentrated to give 2-thienylacetic acid polyethyleneglycol ester monomethyl ether (n=4 to 13, mainly n=8).

II. Esters of other acids.

By ester replacement using a method similar to (1) to (5) above, the following compounds can be obtained:
1. Phenylacetic acid tetraethyleneglycol ester.
2. Phenoxyacetic acid tetraethyleneglycol ester.
3. Tetrazolylacetic acid pentaethyleneglycol ester monomethyl ether.
4. Phenylglycin diethyleneglycol ester monomethyl ether.

What is claimed is:

1. A process for the synthesis of a penicillin or cephalosporin comprising the steps of:
subjecting an amine of the formula:

H$_2$N—Q optionally in an enzymatically acceptable conventional salt or ester form to enzymatic catalysis in the presence of an acylase and in the presence of an ester of the formula:

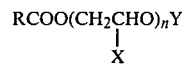

wherein Q is a group of the formula:

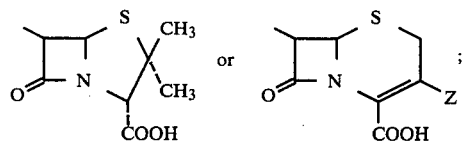

Z is hydrogen, halogen, or a group which consisting of 1 to 7 carbon atoms selected from the group consisting of methyl, lower alkoxy, monocyclic (O, N or S)-heterocyclic thio, monocyclic lower aralkyl, lower alkanoyloxy, lower alkanoyloxy-lower alkyl, monocyclic (O, N or S)-heterocyclic thio-lower alkyl, or pyridinium-lower alkyl, optionally substituted with lower alkyl, carboxy-lower alkyl, lower alkoxy, carbamoyl or halogen; RCO, which contains 1 to 15 carbon atoms, is lower alkanoyl, lower alkenoyl, monocyclic lower aralkanoyl, monocyclic aryloxylower alkanoyl, (O, N or S)-heterocyclic-lower alkanoyl, (O,N or S)-heterocyclic thio-lower alkanoyl, cyanoacetyl, cyanomethylthioacetyl, monocyclic arylglycyl, monocyclic cycloalkenylglycyl, monocyclic arylglycolyl, N-acylarylglycyl, monocyclic arylmalonyl or arylsulfoalkanoyl, optionally substituted with lower alkyl, aminomethyl, halogen, hydroxy, lower alkanoyloxy or lower alkoxy; X is hydrogen, lower alkyl or hydroxymethyl; Y is hydrogen or lower alkyl; and n is an integer of from 1 to 20, to form a penicillin or cephalosporin of the formula:

RCONH—Q wherein R and Q are as defined above.

2. A process according to claim 1, wherein said acylase is an amido-acylase of bacterial or fungal origin.

3. A process according to claim 1, wherein said acylase is an immobilized acylase.

* * * * *